United States Patent
Jin et al.

(10) Patent No.: US 12,236,630 B2
(45) Date of Patent: Feb. 25, 2025

(54) ROBOTIC SURGERY DEPTH DETECTION AND MODELING

(71) Applicant: Verily Life Sciences LLC, South San Francisco, CA (US)

(72) Inventors: Xing Jin, San Jose, CA (US); Caitlin Donhowe, Mountain View, CA (US); Martin Habbecke, Palo Alto, CA (US); Joëlle Barral, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 440 days.

(21) Appl. No.: 16/949,786

(22) Filed: Nov. 13, 2020

(65) Prior Publication Data

US 2021/0145523 A1 May 20, 2021

Related U.S. Application Data

(60) Provisional application No. 62/935,824, filed on Nov. 15, 2019.

(51) Int. Cl.
*G06T 7/73* (2017.01)
*A61B 1/00* (2006.01)
(Continued)

(52) U.S. Cl.
CPC ........... *G06T 7/73* (2017.01); *A61B 1/00149* (2013.01); *A61B 1/00193* (2013.01);
(Continued)

(58) Field of Classification Search
CPC ............ A61B 2034/105; A61B 34/20; A61B 1/00149; A61B 1/00193; A61B 1/04;
(Continued)

(56) References Cited

U.S. PATENT DOCUMENTS

| 8,147,503 B2 | 4/2012 | Zhao et al. |
| 2008/0004603 A1* | 1/2008 | Larkin .................. A61B 34/10 606/1 |

(Continued)

FOREIGN PATENT DOCUMENTS

| JP | 5373263 | 9/2013 |
| KR | 101881620 | 7/2018 |

OTHER PUBLICATIONS

International Application No. PCT/US2020/060456, International Search Report and Written Opinion, mailed Apr. 12, 2021, 24 pages.

(Continued)

*Primary Examiner* — John D Li
(74) *Attorney, Agent, or Firm* — Kilpatrick Townsend & Stockton LLP

(57) ABSTRACT

Systems and methods for depth detection and virtual modeling using surgical robots during a surgical procedure are described. The robotic surgical systems include robotic arms with interchangeable surgical tools. An endoscope at the end of one of the robotic arms includes a depth sensor for detecting a distance from the camera to patient anatomy. The depth data and image data are used to generate a feature model of the patient anatomy for reference by a surgeon. The feature model is displayed to the surgeon in an augmented reality view with preoperative and intraoperative images mapped thereon for reference and guidance of a surgical procedure.

17 Claims, 8 Drawing Sheets

(51) Int. Cl.
*A61B 34/00* (2016.01)
*A61B 34/10* (2016.01)
*A61B 34/20* (2016.01)
*A61B 34/30* (2016.01)
*A61B 90/00* (2016.01)

(52) U.S. Cl.
CPC ........ *A61B 34/20* (2016.02); *A61B 2034/105* (2016.02); *A61B 2034/2051* (2016.02); *A61B 2034/2057* (2016.02); *A61B 2034/2063* (2016.02); *A61B 2034/2065* (2016.02); *A61B 2034/252* (2016.02); *A61B 2034/301* (2016.02); *A61B 2090/365* (2016.02); *A61B 2090/374* (2016.02); *A61B 2090/3762* (2016.02); *A61B 2090/378* (2016.02)

(58) Field of Classification Search
CPC .... A61B 2034/2051; A61B 2034/2057; A61B 2034/2063; A61B 2034/2065; A61B 2034/252; A61B 2034/301; A61B 2090/365; A61B 2090/374; A61B 2090/3762; A61B 2090/378
See application file for complete search history.

(56) References Cited

U.S. PATENT DOCUMENTS

| | | | |
|---|---|---|---|
| 2016/0270861 A1* | 9/2016 | Guru | G09B 23/28 |
| 2018/0139392 A1* | 5/2018 | Rauniyar | A61B 1/063 |
| 2018/0325618 A1* | 11/2018 | Justin | A61B 90/37 |
| 2019/0254754 A1 | 8/2019 | Johnson et al. | |
| 2020/0000399 A1* | 1/2020 | Andersen | A61B 8/5207 |
| 2020/0015910 A1* | 1/2020 | Azizian | A61B 34/20 |
| 2020/0110936 A1* | 4/2020 | Hares | A61B 1/3132 |
| 2021/0059762 A1* | 3/2021 | Ng | A61B 5/7425 |

OTHER PUBLICATIONS

Oliveira et al., "Medical Image Registration: a Review", Computer Methods in Biomechanics and Biomedical Engineering; vol. 17; Issue 2, Feb. 18, 2021, 49 pages.

PCT/US2020/060456 , "Invitation to Pay Additional Fees and, Where Applicable, Protest Fee", Feb. 18, 2021, 6 pages.

* cited by examiner

ROBOTIC SURGERY DEPTH DETECTION AND MODELING

CROSS-REFERENCE TO RELATED APPLICATIONS

This application claims priority to U.S. Provisional Patent Application No. 62/935,824, filed Nov. 15, 2019, titled "Robotic Surgery Depth Detection and Modeling," the entirety of which is hereby incorporated by reference.

BACKGROUND

In recent years, robotic surgeries have become increasingly popular because of their advantages over traditional human-operated open surgeries. Surgical tools used in robotic surgeries enable a human surgeon to have improved levels of dexterity, range of motion, and precision. In most robotic surgical systems, these tools are connected to robotic arms and interchangeable depending on the surgery to be performed.

BRIEF SUMMARY

Various examples are described including systems, methods, and devices relating to depth detection and modeling using surgical robots during a surgical procedure.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method including receiving procedure type data describing a procedure to be performed and receiving preoperative image data corresponding to preoperative imaging of a surgical location, the surgical location based on the procedure type data. The computer-implemented method also includes receiving image data from a camera connected to a robotic arm of a robotic surgical system and receiving kinematic data describing a position of the robotic arm in relation to the surgical location. The computer-implemented method further includes generating a feature model of the surgical location based on the image data and the kinematic data and generating a image-mapped feature model by mapping the image data onto the feature model. The computer-implemented method includes determining a sequence of procedure steps based on the procedure type data and providing, for display at a display device, the image-mapped feature model and the sequence of procedure steps. Other embodiments of this aspect include corresponding computer systems, apparatus, and computer programs recorded on one or more computer storage devices, each configured to perform the actions of the methods.

Another general aspect includes a robotic surgical system including a plurality of robotic arms to perform a surgical procedure, a camera positioned on a first robotic arm of the plurality of robotic arms, a display device to display output from the camera, one or more processors, and one or more non-transitory computer-readable media including processor-executable instructions that, when executed by the one or more processors, cause the one or more processors to perform a number of operations. The operations include receiving procedure type data describing a procedure to be performed and receiving preoperative image data corresponding to preoperative imaging of a surgical location, the surgical location based on the procedure type data. The operations also include receiving image data from a camera connected to a robotic arm of a robotic surgical system and receiving kinematic data describing a position of the robotic arm in relation to the surgical location. The operations further include generating a feature model of the surgical location based on the image data and the kinematic data and generating a image-mapped feature model by mapping or overlaying the image data onto the feature model. The operations include determining a sequence of procedure steps based on the procedure type data and providing, for display at a display device, the image-mapped feature model and the sequence of procedure steps.

Another general aspect includes a computer-implemented method including receiving first image data from a camera connected to an end of a robotic arm of a robotic surgical system, and receiving kinematic data describing a position of the end of the robotic arm in relation to a surgical location. The computer-implemented method also includes generating a feature model representing the surgical location based on the first image data and the kinematic data. The computer-implemented method also includes receiving second image data from the camera and updating the feature model based on the second image data to produce an updated feature model of the surgical location. The computer-implemented method also includes providing, for display at a display device, the updated feature model. Other embodiments of this aspect include corresponding computer systems, apparatus, and computer programs recorded on one or more computer storage devices, each configured to perform the actions of the methods.

Another general aspect includes a robotic surgical system including a plurality of robotic arms to perform a surgical procedure, a camera positioned at an end of a first robotic arm of the plurality of robotic arms, a display device to display output from the camera, one or more processors, and one or more non-transitory computer-readable media including computer-executable instructions that, when executed by the one or more processors, cause the one or more processors to perform operations. The operations include receiving first image data from a camera connected to an end of a robotic arm of a robotic surgical system, and receiving kinematic data describing a position of the end of the robotic arm in relation to a surgical location. The operations also include generating a feature model representing the surgical location based on the first image data and the kinematic data. The operations also include receiving second image data from the camera and updating the feature model based on the second image data to produce an updated feature model of the surgical location. The operations also include providing, for display at a display device, the updated feature model.

Another general aspect includes one or more non-transitory computer-readable media including computer-executable instructions that, when executed by one or more computing systems, cause the one or more computing systems to receive procedure data corresponding to a type of procedure and a surgical location and receive preoperative image data corresponding to preoperative imaging of the surgical location. The instructions further cause the computing systems to receive first image data from a camera connected to an end of a robotic arm and generate a feature model of the surgical location based on the first image data. The instructions further cause the computing systems to generate an image-mapped feature model by mapping the first image data onto the feature model. The instructions further cause the computing systems to receive second image data from the camera, the second image data obtained by the camera during the procedure. The instructions further cause the computing systems to update the image-mapped feature model based on the second image data to produce an updated image-mapped feature model of the surgical location. The instructions further cause the computing systems to provide, for display at a display device, the updated image-mapped feature model.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
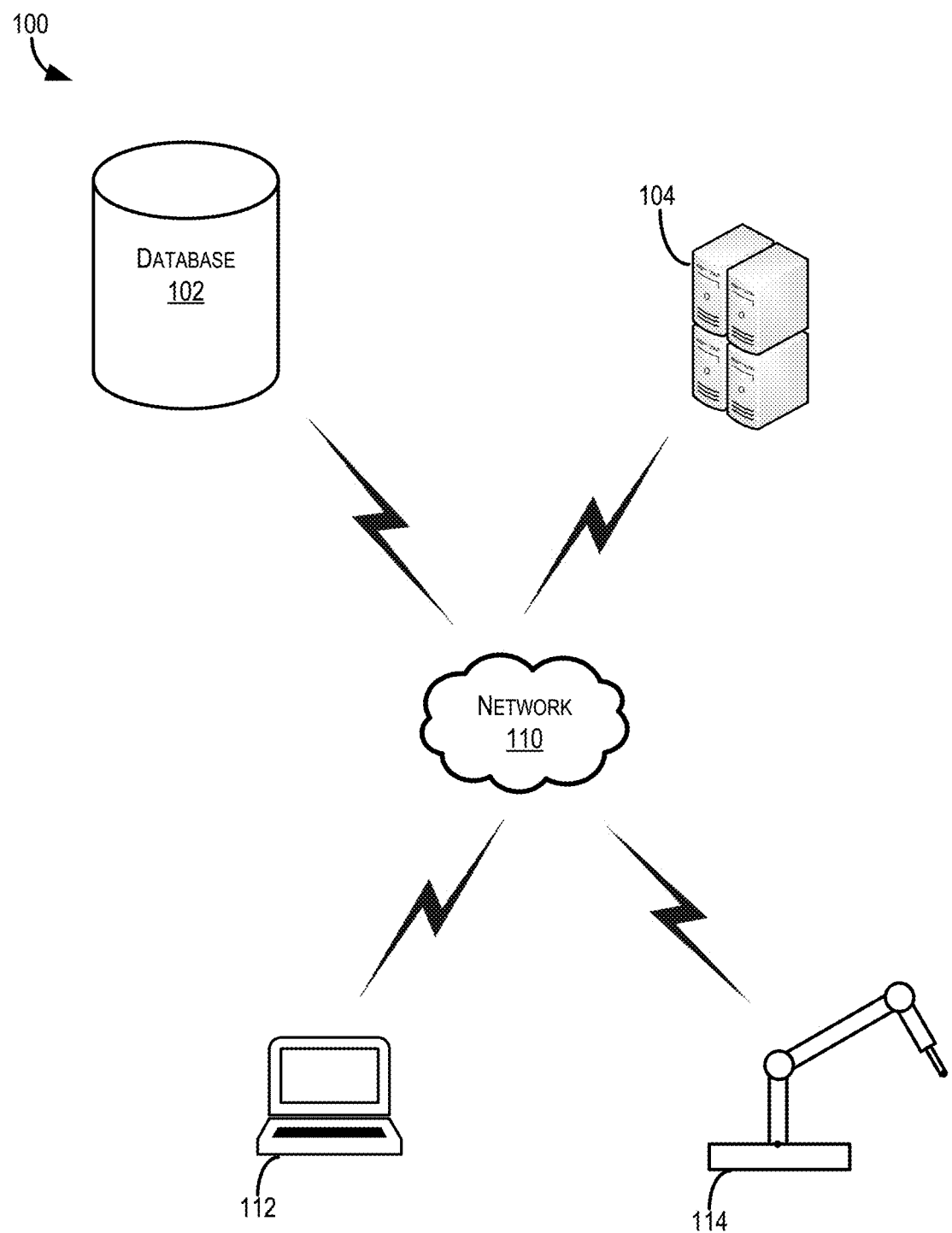
FIG. 1 illustrates a block diagram illustrating an example system for depth detection and modeling in robotic surgery videos, according to at least one example.

Examples are described in the context of configuring a surgical robot at the start of and throughout surgical procedures. Those of ordinary skill in the art will realize that the following description is illustrative only and is not intended to be in any way limiting. For example, the techniques described in this description may be used to model patient anatomy for surgical planning and for guidance during surgical procedures. Though examples and techniques are described with reference to surgical robot configurations, the described methods and systems may also be implemented in other robotic systems such as robotic systems used in assembly processes or other user-controlled robotic systems. Reference will now be made in detail to implementations of examples as illustrated in the accompanying drawings. The same reference indicators will be used throughout the drawings and the following description to refer to the same or like items.

In the interest of clarity, not all of the routine features of the examples are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a robotic surgical system includes one or more robotic arms, each having a surgical tool connected to it. A camera, e.g., an endoscope, is connected to one of the robotic arms to capture images or videos of a surgical procedure performed using the surgical tools. A depth sensor also captures depth data describing a depth of different portions of the field of view of the endoscope. Image data and depth data gathered by a camera outfitted with a depth sensor provides accurate dimensions and distances to patient anatomy. The robotic surgical system also includes a surgeon console for managing operation of the robotic arms (e.g., enabling a surgeon to operate the surgical tools). The robotic surgical system also includes a computer system with software that can generate three-dimensional models (3D) (also called "feature models" or "patient anatomy models"). The user can then view these 3D models on the surgeon console. For example, the software may generate the 3D models based on images captured by the endoscope and the depth data.

In this illustrative example, the robotic surgical system models patient anatomy. For example, the robotic surgical system receives kinematic data for the robotic arms describing the location and orientation of the joints and especially the end of the robotic arm. The robotic surgical system receives the image data from the endoscope and the depth data from the depth sensing device, and uses the data to generate a 3D model (e.g., the patient anatomy model) that represents a patient's internal anatomy. The robotic surgical system also outputs the 3D model to a display or other output device, such as on the surgeon console. The robotic surgical system can manipulate the 3D model and updating the 3D model as the surgery advances. For example, the robotic surgical system may update the 3D model as a portion of the anatomy is removed (e.g., as part of a biopsy), and provide an updated representation of the model at the display for viewing by the surgeon.

The robotic surgical system also maps or overlays images to the patient model. Mapping the images to the patient model results in generating a photorealistic rendering of the patient anatomy onto the 3D model. In an example, the system identifies features or edges in preoperative images and matches those features to edges or features in the 3D model. The images are then mapped onto the 3D model to generate the photorealistic rendering of the patient anatomy in the 3D model. The robotic surgical system may also display the 3D model, or a semitransparent form of the 3D model on an augmented reality (AR) display of the surgical procedure, tracking the progress and stages of the surgical procedure with the AR display and 3D model for ease of reference for the surgeon.

The systems and methods of this disclosure increase the efficiency and accuracy of surgical procedures performed with a robotic surgical system by gathering, with a depth sensor connected to an endoscope, depth data to generate accurate anatomy models so the surgeon is able to properly plan and perform the surgical procedure safely. The systems and methods may aid the surgeon in both planning and performing difficult operations and ensure that the unique patient anatomy is planned for and the procedure is adapted for the individual patient. The surgeon may use the model to track progress of the procedure by including a transparent view of the original anatomy to compare against the current anatomy and visually represent, for example, a portion of anatomy removed during the surgery. The surgeon may also observe the model from different angles and at different levels of zoom to better understand the particular procedure site. The systems and methods aid in preventing collisions of robotic surgical systems with patient anatomy, as described above, and prevent possible inadvertent injury to the patient by colliding the robotic arms with sensitive anatomy inadvertently while it is out of the field of view of the endoscope. To accomplish this, the surgeon may view, or be able to keep track of, anatomy that is not visible in a present field of view of the endoscope to prevent accidental collisions of the robotic arms with that non-visible anatomy. This is accomplished by maintaining a model of all of the patient anatomy viewed by the endoscope and the depth sensor and presenting the model in a virtual reality display that the surgeon can navigate independently of the controls of the robotic arms. Rather than ceasing to re-gather data relating to the procedure, the data is gathered in real-time, providing up to date information about the procedure, speeding up surgical procedures while still maintaining safety.

This illustrative example is given to introduce the reader to the general subject matter of the disclosure though the disclosure is not limited to this example. The following sections describe various additional non-limiting examples and techniques relating to depth measurement and anatomy modeling during surgical procedures.

Turning now to the figures, FIG. 1 illustrates a block diagram of a system 100 for depth detection in robotic surgery videos as well as patient anatomy modeling, according to at least one example. The system 100 includes a computing device 104, a robotic surgical device 114, a surgical console 112, and a database 102. The robotic surgical device 114 includes any suitable number of robotic arms, as described in additional detail with respect to FIG. 2. The surgical console 112 is a device at which a user controls the robotic surgical device 114 and views a display showing the field of view of a camera of the robotic surgical device 114 and may include other components as described below with respect to FIG. 2.

The computing device 104 is any suitable electronic device (e.g., personal computer, hand-held device, server computer, server cluster, virtual computer, etc.) configured to execute computer-executable instructions to perform methods according to this disclosure. The components of the system 100 are connected via one or more communication links with the network 110. In some examples, the computing device 104 may be incorporated into or part of the surgical console 112. The computing device 104, the database 102, and the surgical console 112 may be in network communication with each other as shown through network 110. The network 110 includes any suitable combination of wired, wireless, cellular, personal area, local area, enterprise, virtual, or other suitable network.

The computing device 104 receives image data and depth data from the robotic surgical device and generates a model of the patient anatomy viewed by an endoscope of the robotic surgical device. The model of the patient anatomy is of the surgical site in addition to all of the anatomy previously viewed by the camera. The computing device 104 maps image data from the database 102 onto the model to generate a photorealistic view of the patient anatomy. The computing device 104 then displays the model at the surgical console 112 for use by a surgeon.

Figure 2:
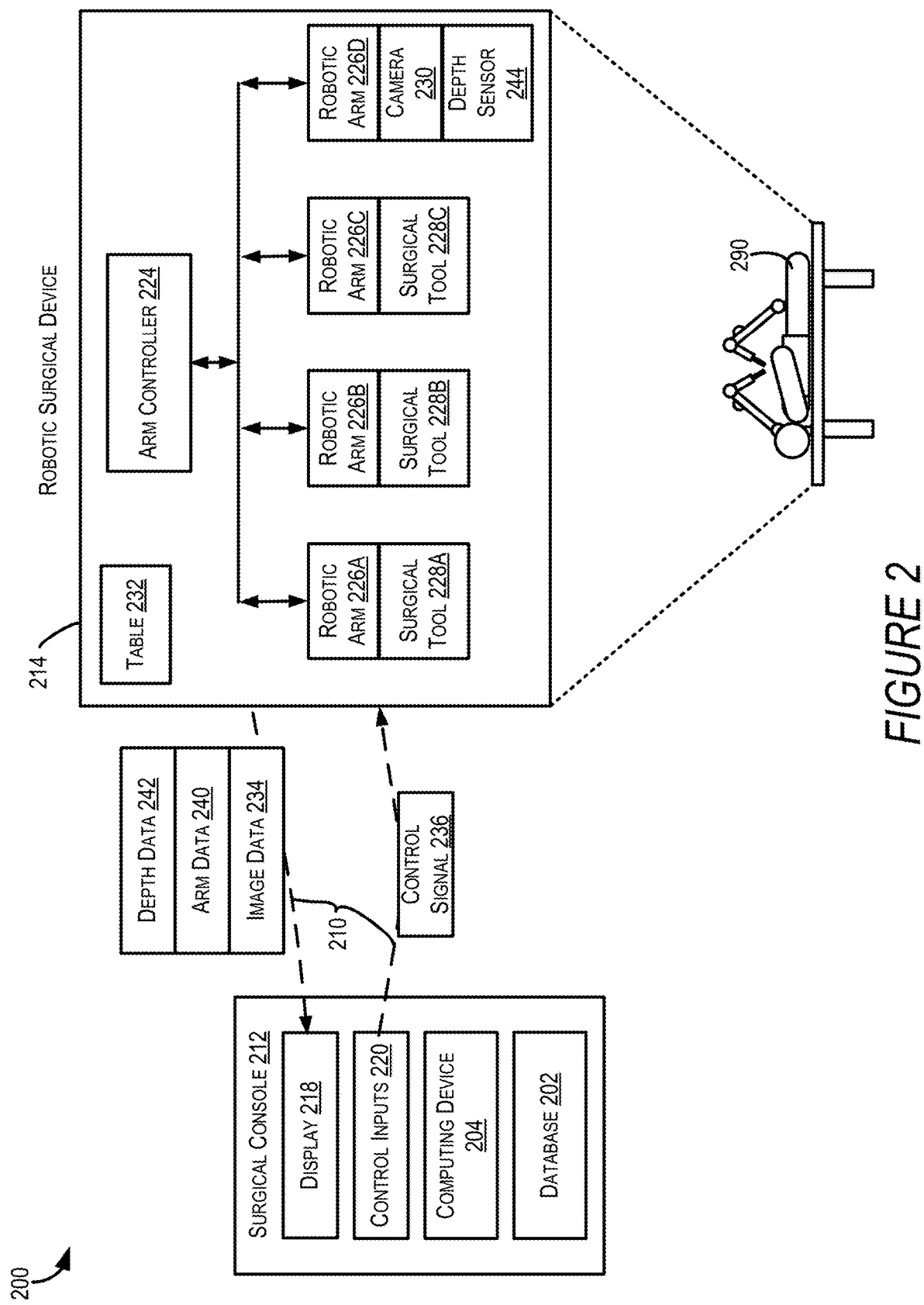
FIG. 2 illustrates an example system for depth detection and modeling in robotic surgery videos, according to at least one example.

FIG. 2 illustrates a system 200 for depth detection in robotic surgery videos as well as patient anatomy modeling, according to at least one example. In the system 200, the robotic surgical device 214 is configured to operate on a patient 290. The system 200 also includes a surgical console 212 connected to the robotic surgical device 214 and configured to be operated by a surgeon to control the robotic surgical device 214 to perform a surgery. The system 200 might also include additional stations (not shown in FIG. 2) that can be used by other personnel in the operating room, for example, to view surgical information, video, etc., sent from the robotic surgical device 214. The robotic surgical device 214, the surgical console 212, and other stations can be connected directly or through the network 210, such as a local-area network ("LAN"), a wide-area network ("WAN"), the Internet, or any other networking topology known in the art that connects the robotic surgical device 214, the surgical console 212 and other stations.

The robotic surgical device 214 can be any suitable robotic system that can be used to perform surgical procedures on the patient 290. The robotic surgical device 214 includes one or more robotic arms 226A-D (which may be referred to individually as a robotic arm 226 or collectively as the robotic arms 226) connected to a base such as a table 232. The robotic arms 226 may be manipulated by control inputs 220, which may include one or more user interface devices, such as joysticks, knobs, handles, or other rotatable or translatable devices to effect movement of one or more of the robotic arms 226. The robotic surgical device 214 includes an arm controller 224 to control the robotic arms 226 based on the control inputs 220. The arm controller 224 controls the positioning and movement of the robotic arms 226 based on a control signal 236 from the surgical console 212 generated by the control inputs 220. The robotic arms 226A-D may be equipped with one or more surgical tools 228 to perform aspects of a surgical procedure. For example, the robotic arms 226A-C may be equipped with surgical tools 228A-C, (which may be referred to individually as a surgical tool 228 or collectively as the surgical tools 228). The surgical tools 228 can include, but are not limited to, tools for grasping for holding or retracting objects, such as forceps, graspers and retractors, tools for suturing and cutting, such as needle drivers, scalpels and scissors, and other tools that can be used during a surgery. Each of the surgical tools 228 can be controlled by the surgeon through the surgical console 212 including the control inputs 220.

Different surgical devices may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one robotic surgical device 214 is depicted, any suitable number of surgical devices 214 may be employed within system 200.

The robotic surgical device 214 is also equipped with one or more cameras 230, such as an endoscope, configured to provide a view of the operating site to guide the surgeon during the surgery. In some examples, the camera 230 can be attached to one of the robotic arms 226D. In some examples, the camera 230 can be attached to a mechanical structure of the robotic surgical device 214 that is controlled separately from the robotic arms 226 or is stationary with respect to the robotic surgical device 214.

The robotic surgical device 214 also includes a depth sensor 244 attached to one of the robotic arms 226D. The depth sensor 244 senses or detects a depth or distance from the camera 230 to portions of the patient's anatomy. The depth sensor 244 is aligned with the field of view of the camera 230 so depth data 242 relayed from the depth sensor 244 is related to visible patient anatomy. The depth sensor 244 is a time-of-flight sensor which emits an infrared light pulse and detects return time for the light pulse to return to the depth sensor 244. In some instances, the depth sensor 244 may be an ultrasound sensor, a radio detection and ranging sensor, a light detection and ranging sensor, a second camera implemented as a stereo camera, or any other suitable sensor suitable for measuring depth. Stereo images from the camera 230 and the second camera may be used to generate a depth map or three-dimensional image of the field of view which provides distances from the camera 230 to portions of the patient anatomy. Stereo cameras and stereo image reconstruction to generate the patient anatomy model relies on a known distance between the stereo cameras remaining fixed. Stereo image reconstruction also relies on a computing device 204 comparing the field of view captured by each camera of the stereo camera and observing relative positions of objects in each field of view. Suitable stereo reconstruction techniques may be used to determine distances to points on objects within the captured images, such as dense stereo matching techniques. The depth sensor 244 communicates depth data 242 to the computing device 204 for processing and use by the computing device 204.

The surgical console 212 includes a display device 218 for providing a feed of image data 234 from the camera 230 as well as patient anatomy models and depth information gathered by the system 200. The image data 234 is transferred to the surgical console 212 over the network 210 along with arm data 240 describing the position of each of the robotic arms 226. The computing device 204 may be the computing device 104 described in FIG. 1 and is shown included in the surgical console 212 but may also be located remotely of the surgical console 212 as described above.

The display device 218 may display surgical procedure steps for reference by the surgeon based on surgical procedure steps accessed by the computing device 204 from the database 202. The surgical procedure steps may include a predetermined series of surgical steps stored in the database 202 and displayed sequentially on the display 218. The surgical console 212 may allow the surgeon to indicate a current step being performed and view upcoming steps including movements and positions of the robotic arms 226 to perform the procedure steps.

It should be understood that although FIGS. 1 and 2 illustrate various components of the systems 100, 200, some elements of the system 200, such as the database 202 or the modeling device 500 or image mapping device 600 described below with respect to FIGS. 5 and 6, that are included in the computing device 204 or in communication over the network 210, one or more of these devices may be implemented in different ways within the system 200. For example, the functionality described above need not be separated into discrete devices, or some or all of such functionality may be located on a computing device separate from the robotic surgical device 214, the surgical console 212, or the computing device 204 such as a central controlling device connected to the robotic surgical device 214 directly or through the network 210 and configured to control the components of the system 200.

Figure 3:
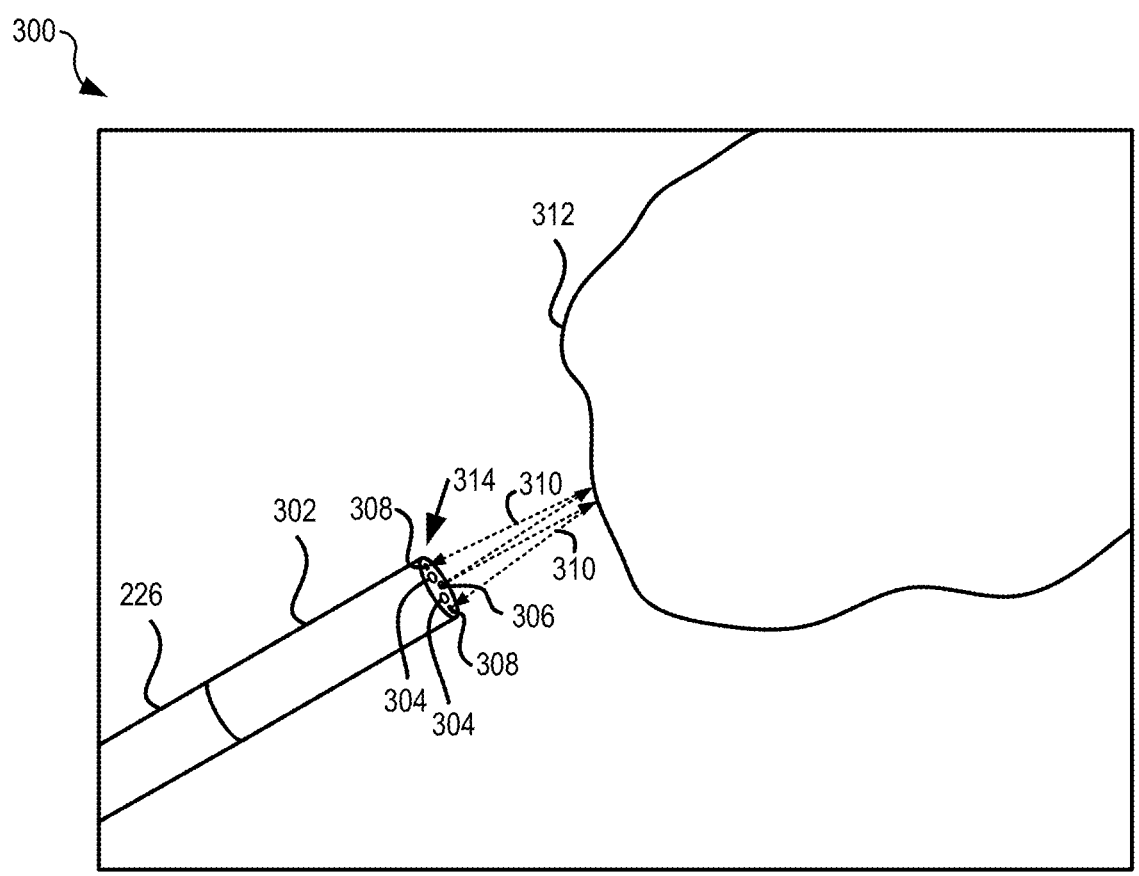
FIG. 3 illustrates a depiction of an endoscope for depth sensing during robotic surgery, according to at least one example.

FIG. 3 shows a view 300 of a robotic arm 226 including an endoscope 302 having a depth sensor 314 included for viewing and capturing data of a user's anatomy 312. The endoscope 302 includes cameras 304 separated by a set distance as a stereo endoscope, which can be used to generate a three-dimensional view and to determine a distance from the endoscope 302 to an object within the field of view of the endoscope 302. The distance is calculated from differences between corresponding pixels in the images captured by each of the cameras 304 and additional data such as the focal length of the cameras and the distance between the cameras.

The endoscope 302 also includes a depth sensor 314 including an emitter 306 and detectors 308. In one example, the emitter 306 emits a light 310 such as an infrared light source, though in some examples, the emitter may emit ultrasound. The detectors 308 detect reflections of the light 310 off of anatomy 312 the computing device 204 uses a time-of-flight method to determine the distance from the emitter to the object in view of the endoscope 302.

In some examples, the depth sensor 314 may be other types of depth sensors besides that described above. For example, the stereo endoscope with the stereo cameras may function as the depth sensor itself, the emitter may illuminate the field of view with a sheet of light through sheet of light triangulation as known to those with skill in the art. In some examples, the depth sensor may also use structured light by emitting a particular known pattern of light and observing deviations and distortions in the pattern as it intersects other objects. Still other depth sensors may employ ultrasound or radar emitters and detectors. Other depth detecting methods may be implemented, including depth detecting methods using images that do not require dedicated depth-sensing hardware or elements. For example, a single camera may capture multiple images from known locations within a surgical site, e.g., based on kinematic data, and depths of objects within the environment may be determined based on those multiple images, such as based on pixel matching or other known techniques.

Figure 4:
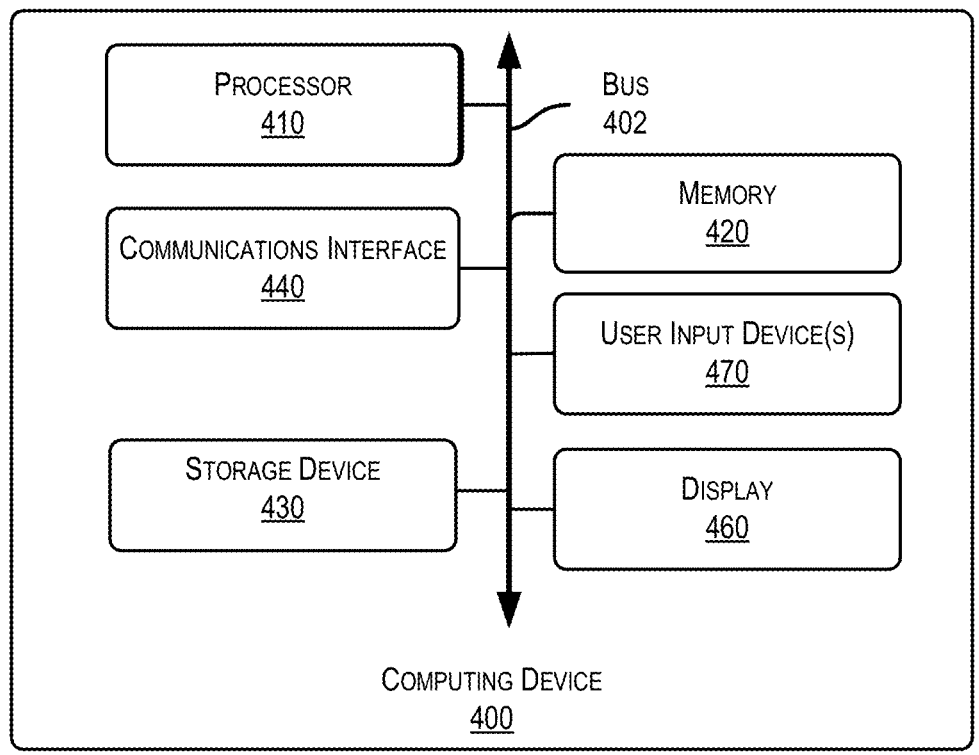
FIG. 4 illustrates a simplified block diagram depicting an example architecture for implementing one or more example methods according to the disclosure.

Referring now to FIG. 4, FIG. 4 shows computing device 400 suitable for use in example systems or methods for depth detection in robotic surgery systems, according to at least one example. For example, computing device 400 may be the computing device 104, 204 of FIG. 1 or 2, respectively. Computing device 400 includes a processor 410 which is in communication with the memory 420 and other components of the computing device 400 using one or more communications buses 402. The processor 410 is configured to execute processor-executable instructions stored in the memory 420 to determine depths, geometry, and model patient anatomy according to different examples, such as part or all of the example processes 700, 800, and 900 described below with respect to FIGS. 7, 8, and 9. The computing device 400, in this example, also includes one or more user input devices 470, such as a keyboard, mouse, touchscreen, microphone, etc., to accept user input. The computing device 400 also includes a display to provide visual output to a user.

The computing device 400 can include or be connected to one or more storage devices 430 that provides non-volatile storage for the computing device 400. The storage devices 430 can store system or application programs and data used by the computing device 400, such as devices implementing the functionalities provided by the modeling device 500 and the image mapping device 600. The storage devices 430 might also store other programs and data not specifically identified in this description.

The computing device 400 also includes a communications interface 440. In some examples, the communications interface 440 may enable communications using one or more networks, including a LAN; WAN, such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems are described in terms of software executing on various machines, the methods and systems may also be implemented as specifically configured hardware, such as field-programmable gate array ("FPGA") specifically to execute the various methods. For example, examples may be implemented in digital electronic circuitry, or in computer hardware, firmware, software, or in a combination thereof. In one example, a device may include a processor or processors. The processor includes a computer-readable medium, such as a random access memory ("RAM") coupled to the processor. The processor executes processor-executable program instructions stored in memory, such as executing one or more computer programs. Such processors may include a microprocessor, a digital signal processor ("DSP"), an application-specific integrated circuit ("ASIC"), field programmable gate arrays ("FPGAs"), and state machines. Such processors may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

Such processors may include, or may be in communication with, media, for example computer-readable storage media, that may store instructions that, when executed by the processor, can cause the processor to perform the steps described as carried out, or assisted, by a processor. Examples of computer-readable media may include, but are not limited to, an electronic, optical, magnetic, or other storage device that may provide a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code executable to carry out one or more of the methods (or parts of methods) discussed below with respect to FIGS. 7 through 9.

Figure 5:
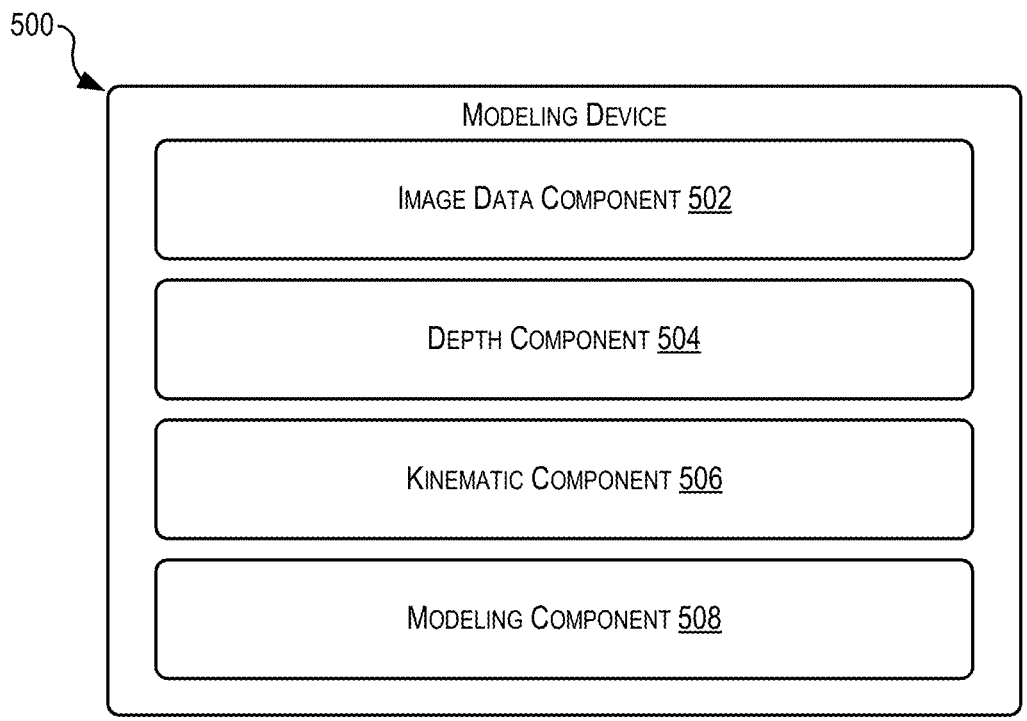
FIG. 5 illustrates a simplified block diagram depicting elements for modeling patient anatomy, according to at least one example.

FIG. 5 depicts a block diagram depicting an example modeling device 500, representing an example of a software architecture with components or sub-devices to enable depth detection and modeling of patient anatomy. To this end, the modeling device 500 includes an image data component 502, a depth component 504, a kinematic component 506, and a modeling component 508.

Generally, during a surgical procedure, the modeling device 500 receives image data 234 as well as depth data 242 and generates a model of the patient's anatomy based on the depth data 242 and in some cases also based on the image data 234. In some instances, the depth data 242 may be preprocessed before being used to generate the model, for example, in the case of a stereoscopic endoscope the stereoscopic images may be pre-processed to produce the depth data 242 that is then used by the computing device 204 to generate the model. As described above, the depth data 242 may include a number of different sources and types of data including image data from a depth sensor 244 such as a stereo camera or other depth sensing device. The modeling device 500 models or constructs a patient anatomy model, such as a three-dimensional representation of the anatomy of the patient visible in the field of view of the camera 230 based on the depth data 242. For example, constructing the patient anatomy model may include the modeling device 500 connecting points in three-dimensional space, located by the depth data and the arm data, to form a polygonal mesh. Other modeling techniques known in the art, such as curve modeling, digital sculpting, and point-cloud modeling may be used with the depth data generating the three-dimensional points in space.

The modeling device 500 is also able to update the model of patient anatomy based on further depth data gathered by the depth sensor 244 as the camera 230 is moved during a procedure. To update the patient anatomy model, the modeling device 500 receives the depth data 242 as described already as well as arm data 240 describing the kinematics of the robotic arms 226. The arm data 240 describes the position of the robotic arm 226D that has the camera 230 and depth sensor 244 connected thereto. By using the arm data 240 and the depth data 242 to locate three-dimensional reference points of the patient anatomy, the modeling device 500 is able to generate and update a patient anatomy model of a surgical site from multiple perspectives. For example, with a robotic arm 226 in a single port (e.g., an access port to a surgical site in an abdomen of a patient, such as a trocar), the camera 230 may be moved, rotated, repositioned, or otherwise adjusted to capture a different perspective of the surgical site. In some examples, the camera 230 and the depth sensor 244 may be moved between multiple different surgical ports, such as different trocars located in different positions on the patient, to obtain image data 234 and depth data 242 of the surgical site from the different perspectives available from the different surgical ports. These approaches for gathering additional image data 234 and depth data 242 use the arm data 240 to locate the updated positions and orientations of the camera 230 and the depth sensor 244 with respect to the same reference frame at which initial data was gathered (e.g., prior to the patient anatomy model being first generated). In some examples, the use of arm data 240 and depth data 242 allows the modeling device 500 to accurately track positions and orientations of the cameras and to use depth data 242 from multiple angles and locations to model patient anatomy. Further details regarding the processes performed by the modeling device 500 are described with reference to processes 700, 800, and 900 below.

Turning now to the image data component 502, the image data component 502 interfaces with the camera 230 and the database 202 to access image data 234 for use by the modeling device 500 including intraoperative images from the camera 230 such as stereoscopic images. Intraoperative images captured by the camera 230 may be mapped on the patient anatomy model as described above to provide a photorealistic view of the patient anatomy overlaid on the patient anatomy model. In some instances, the image data component 502 may also access preoperative images captured using x-ray, CAT scan, endoscopes, or other imaging techniques. The image data component 502 alone, or in combination with the database 202, stores information such as the images described above.

The depth component 504 determines a depth or distance to elements of patient anatomy using the depth sensor 244.

As described above, the depth sensor 244 may, in some examples be the camera 230 or a standalone depth sensor. In some examples, the depth sensor 244 may be a dedicated, independent sensor such as those described above with respect to FIG. 3. The depth component 504 receives data, such as depth data 242 or image data from a stereo camera, and determines a depth or distance to patient anatomy with respect to some frame of reference, such as the camera 230.

The kinematic component 506 determines a position and orientation of the camera 230 in a robotic coordinate system based on the kinematics of the robotic arm 226D to which the camera 230 is connected. In some examples, a kinematic chain or model of the robotic arm 226D may be used to determine the position and orientation of the camera 230. The kinematic chain includes successive joint angles and linkage lengths for the robotic arm 226D and through the use of trigonometry, the position of the end of the robotic arm 226D including the camera 230 can be located in a three-dimensional space. The orientation of the camera 230 is likewise determined such that depth data and image data captured by the camera 230 and depth sensor 244 may be pieced together or stitched together to generate an accurate view or model of the patient anatomy, even when the camera 230 moves or rotates. This is because the location and orientation of the camera are known at each point in time and are therefore comparable in a single coordinate system or frame of reference.

The modeling component 508 builds a model representing the patient anatomy within the surgical area based on the depth data 242 and the image data 234. The modeling component uses the depth data 242 to generate the patient anatomy model. The patient anatomy model may be a polygonal mesh, a wireframe model, a collection or cloud point model, or generated by another three-dimensional modeling technique known in the art. The modeling component uses the arm data 240 and the depth data 242 to generate the patient anatomy model from different angles, as the arm data 240 and the arm kinematics can be used to combine depth data 242 from different locations of the camera 230. The modeling component 508 can update or add to the patient anatomy model as new data is gathered by the camera 230 and the depth sensor 244. For example, a shell of a patient anatomy model representing one half of an organ may be generated initially and, as the camera 230 is moved to different locations, the shell may be further refined, updated, and/or expanded to create a more refined version of the patient anatomy model.

In some examples, the modeling component 508 updates the patient anatomy model as a surgical procedure progresses. For example, when a procedure requires removal of a portion of anatomy, the patient anatomy model may be updated to show the portion that has been removed and the portion which is yet to be removed. This feature may be implemented in some examples to guide or provide instruction to a user. For example, the patient anatomy model may show a portion of anatomy to be removed on the display device 218 in red, with portions of the anatomy that are to remain untouched shown on the display device 218 in a different color such as green.

Figure 6:
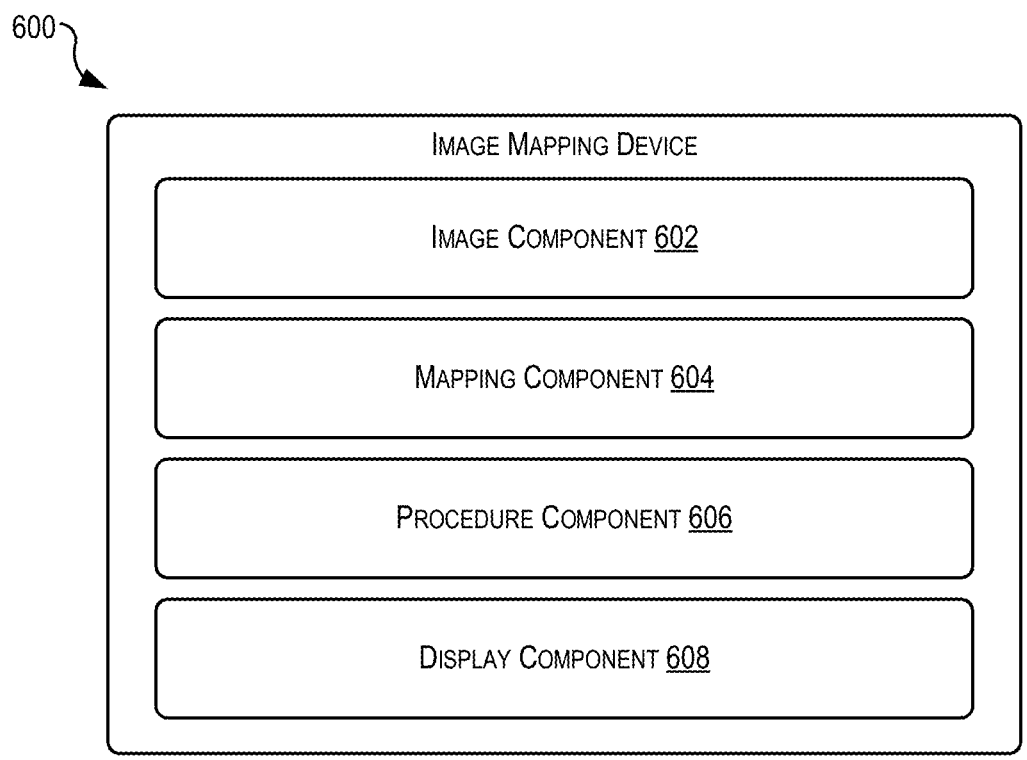
FIG. 6 illustrates a simplified block diagram depicting elements for mapping images to a model of patient anatomy, according to at least one example.

FIG. 6 depicts a block diagram depicting an example image mapping device 600, representing an example of a software architecture with components or sub-devices to enable mapping of image data 234 onto the patient anatomy model generated by the modeling device 500 described above. This mapping may include mapping preoperative imaging or intraoperative images from the camera 230 onto the patient anatomy model to provide a realistic virtual view of the patient anatomy. The image mapping device 600 outputs an image-mapped patient anatomy model, or representation of a patient anatomy model, with the mapped images of the patient anatomy to present a photorealistic model of the patient anatomy. Additionally, the model and the image-mapped model are updated throughout the procedure and the images from camera 230 may be used to update the rendering of the patient anatomy model by mapping the images from camera 230 onto the model during the surgical procedure. To this end, the image mapping device 600 includes an image component 602, a mapping component 604, a procedure component 606, and a display component 608.

Turning now to the image component 602, the image component 602 interfaces with the computing device 204 and the database 202 to access image data 234 for use by the image mapping device 600 including intraoperative images and preoperative images of the patient as described above with respect to FIG. 5.

The mapping component 604 maps images to the patient anatomy model by using a mapping or overlaying method known to those skilled in the art, including image registration techniques. Some example methods include area-based or feature-based methods. In general, one example registration method includes feature detection, feature matching, estimating model transformation, and image resampling and transformation. These methods identify features in the images and model and map the images onto the model, including image transformation, to provide a photorealistic model. Feature detection relies on closed-boundary regions, edges, contours, line intersections, corners, or other easily identifiable features. Feature matching, following feature detection, involves correlating an identified feature in multiple images. Estimating model transformation involves estimating an alignment of the images and the patient anatomy model. Finally, the images are transformed with mapping functions computed by interpolation or other techniques.

The procedure component 606 accesses the database 202 to access a sequence of steps or instructions for the surgical procedure to be performed. The procedure component 606 may receive an input from the surgical console 212 indicating a current status or step of the surgical procedure and convey a next step to be performed for display at the surgical console 212. In an example, the procedure component may include image recognition or pattern recognition software to recognize, automatically, the current status of the surgical procedure based on the patient anatomy model and the arm data 240. For example, the patient anatomy model may represent a portion of anatomy already removed and a portion yet to remove, and the procedure component 606 may generate instructions to convey to the surgeon for proceeding with the next step of the surgical procedure. In some examples, the instructions may be general instructions providing guidance for a surgeon. In some examples, the instructions may include particular movements of the robotic arms 226, such as where to move particular joints and surgical tools 228.

The display component 608 conveys the image-mapped patient anatomy model to the surgical console 212 for display at the display device 218. The image-mapped patient anatomy model may be displayed in augmented reality at the display, with the view of the endoscope including a graphical element representing the image-mapped feature model. The display component 608 may also show the status of the procedure as described above, such as showing a portion of anatomy yet to be removed and a shadow or transparent model of anatomy that has already been removed. The procedure step and the next step of the surgical procedure may also be displayed at the display device 218 with text notifications or other visual displays such as graphical elements.

It should be understood that although FIGS. 5 and 6 illustrate various components, such as the modeling device 500 and the image mapping device 600 that are included in the computing device 204 or in communication over the network 210, one or more of these devices may be implemented in different ways within the system 200. For example, the functionality described above need not be separated into discrete devices, or some or all of such functionality may be located on a computing device remote from the robotic surgical device 214, the surgical console 212, or the computing device 204. For example, the functions described above may be provided by a central controlling device connected to the robotic surgical device 214 directly or through the network 210 and configured to control the components of the system 200.

Figure 7:
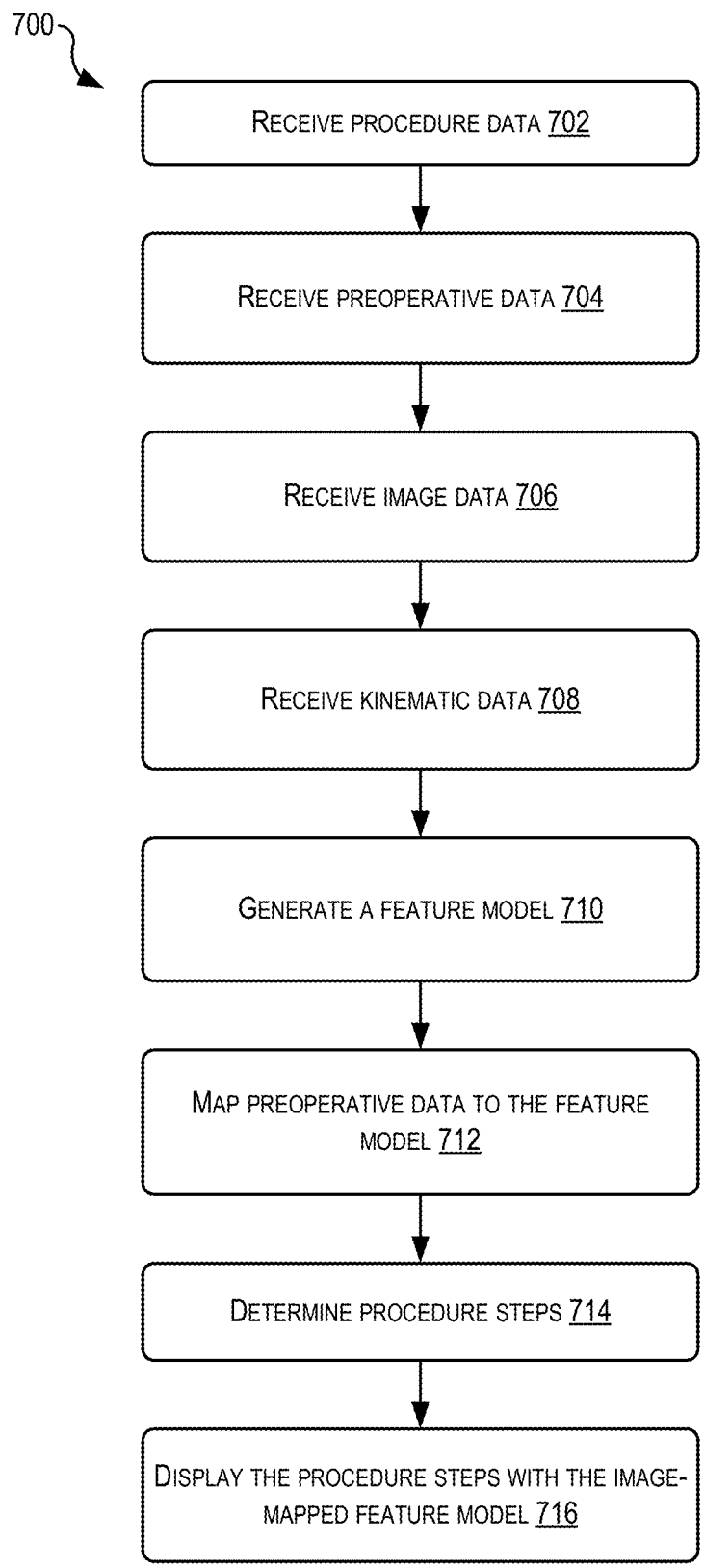
FIG. 7 illustrates an example flow chart depicting an example process for modeling and mapping image data during a robotic surgery, according to at least one example.
Figure 8:
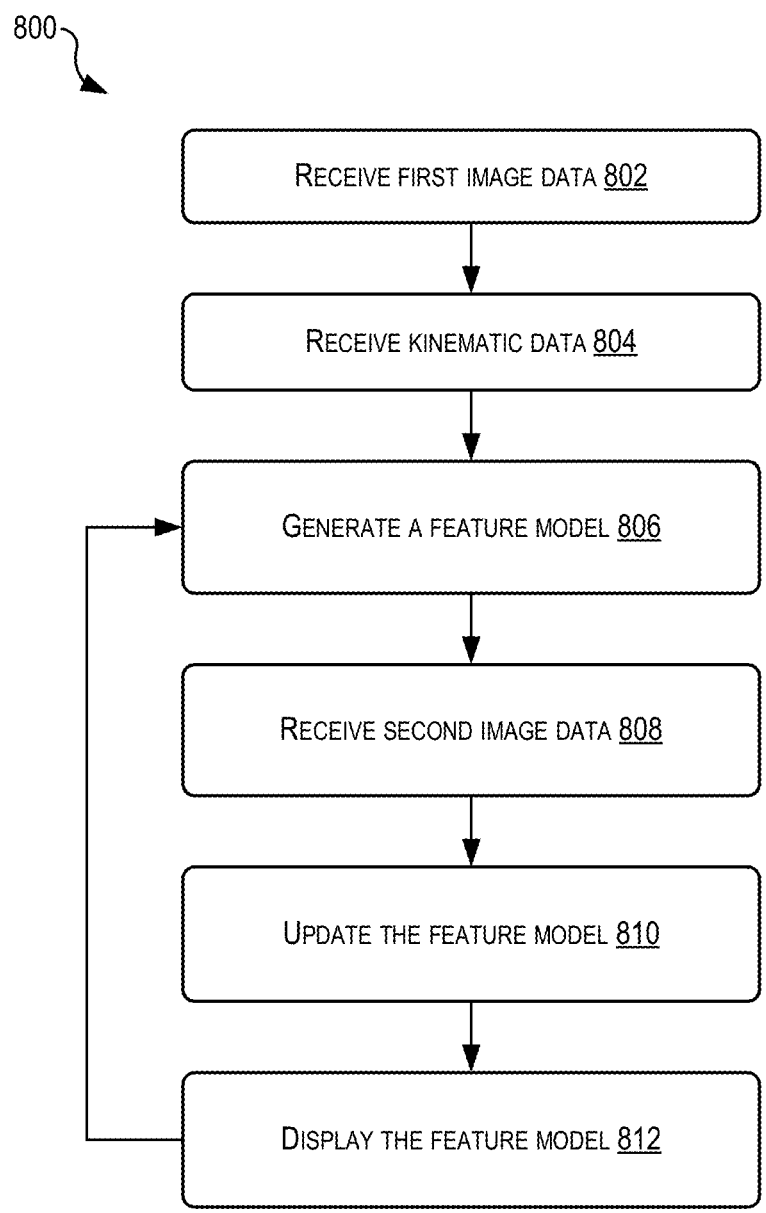
FIG. 8 illustrates an example flow chart for generating an image-mapped model of patient anatomy during a robotic surgery, according to at least one example.
Figure 9:
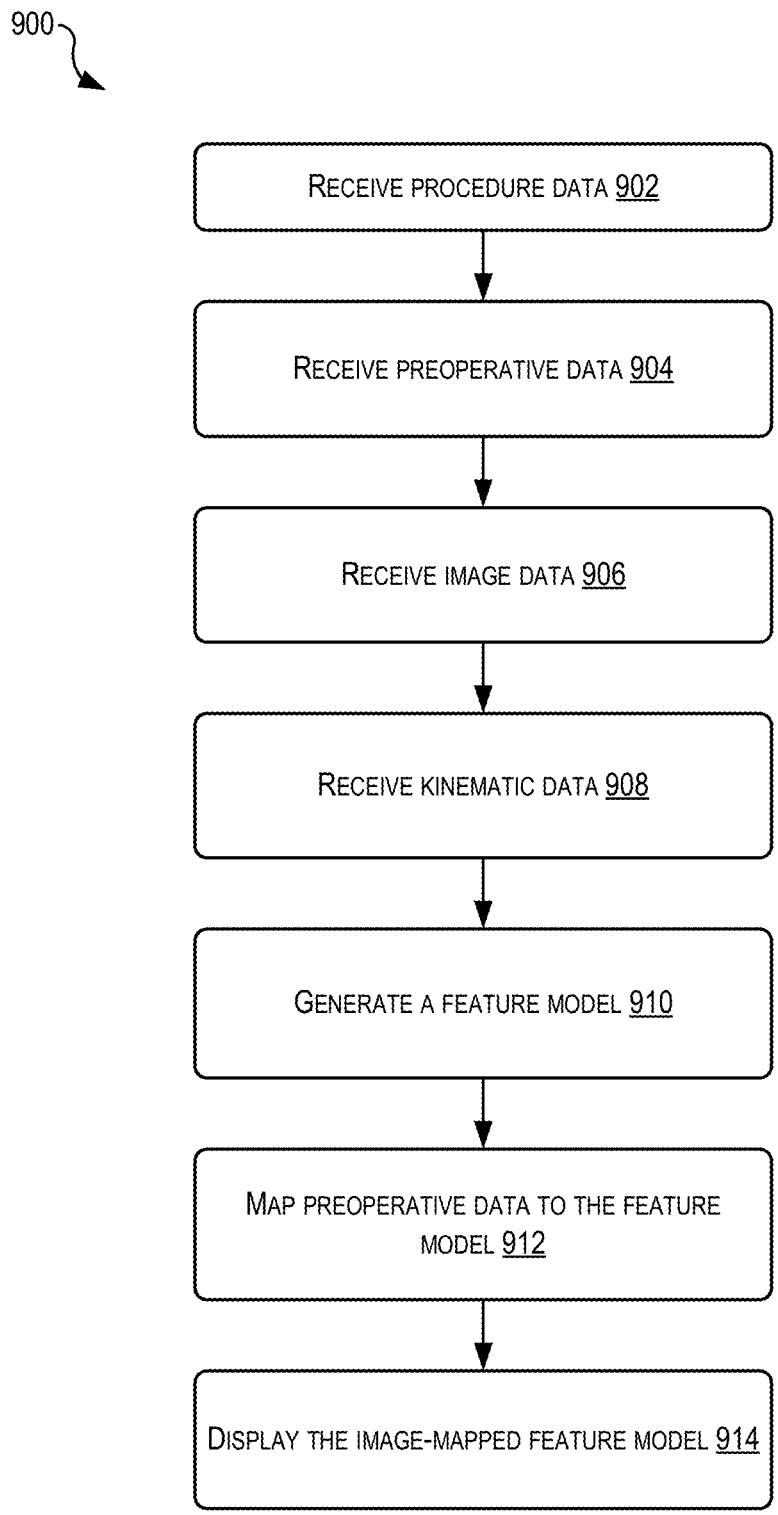
FIG. 9 illustrates an example flow chart for mapping preoperative images to a patient anatomy model during a robotic surgery, according to at least one example.

FIGS. 7-9 illustrate example flow diagrams showing processes 700, 800, and 900, according to at least a few examples. These processes, and any other processes, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

Turning now to FIG. 7, FIG. 7 illustrates an example flow chart depicting a process 700 for depth sensing, modeling, and displaying an up-to-date patient model during a surgical procedure, according to at least one example. The process 700 is performed by the computing device 204, and may be performed by the modeling device 500 and the image mapping device 600, though in some cases may be performed by other software elements of the computing device 204. The process 700 in particular corresponds to generating and presenting an image-mapped feature model and surgical instructions to a surgeon during a surgical procedure.

The process 700 begins at block 702 by the computing device 204 receiving procedure data. The procedure data relates to the surgical procedure to be performed by the robotic surgical device 214 and may be received from a user (e.g., a surgeon or other authorized user) through a user input device of the surgical console 212 or from database 202 where it was previously stored. The procedure data includes data such as the type of procedure (e.g., appendectomy, laparotomy, laparoscopy). The procedure data may include information such as arm data, patient anatomy models, and robotic arm placements during a previous surgical procedure.

At block 704, the computing device 204 receives preoperative data from the database 202. The preoperative data includes preoperative image data such as x-rays or other imaging performed prior to the operation. The preoperative image data may correspond to location of a future surgical site. In some examples, a user may use the computing device 204 to request the preoperative data. In some examples, depending on the procedure data received at block 702 and a patient identifier, the computing device 204 may automatically request the preoperative data relating to the patient and the particular procedure to be performed.

At block 706, the computing device 204 receives image data 234 from the camera 230 depicting an area surrounding the surgical site within the patient's body. The image data 234 may include images from a stereo camera or may include a single image or a stream of sequential images. In some examples, such as when the camera 230 is a stereoscopic camera that functions as the depth sensor 244, the image data from the camera 230 may also include depth data, as described above with respect to FIG. 3. In some examples, such as when a dedicated depth sensor 244 is provided, the process 700 may also include the computing device 204 receiving the depth data from the depth sensor 244.

At block 708, in addition to receiving the image data 234, the computing device 204 receives kinematic data from the robotic surgical device 214. The kinematic data may describe the current position or orientation of the robotic arms 226. The kinematic data received at block 708 may be descriptive of the robotic arm 226D to which the camera 230 is connected.

At block 710, after receiving the depth data, the computing device 204 generates a feature model of the patient anatomy surrounding the surgical site based on the image data 234 and the depth data 242. The feature model may also be generated based on the kinematic data, such as the arm data 240. The feature model is generated by the computing device 204 as described above with respect to the modeling device 500 and may include three-dimensional modeling techniques known in the art based on the data received by the computing device 204.

At block 712, the computing device 204 maps the preoperative data to the feature model generated in block 710. This is performed by the computing device 204 performing image mapping or image registration techniques, such as described above with respect to the image mapping device 600. Block 712 may include the computing device 204 mapping based on feature detection, edge detection, region-mapping, or any other known image mapping or overlaying technique for laying images onto a 3D model. At block 712, the computing devices 204 maps the preoperative data to generate an image-mapped feature model. In some examples, the image data 234 may also be mapped to the feature model, providing an up-to-date image-mapped feature model of the patient anatomy.

At block 714, the computing device 204 determines procedure steps of the surgical procedure based on the procedure data received at block 702 for displaying alongside the 3D model on the display 218. This may also include receiving data relating to a present step of the surgical procedure. This data may be input by a user or may be determined by an algorithm on the computing device, performing a pattern recognition technique to identify, based on the procedure data and the arm data, the current step of the surgical procedure. The kinematic data may be compared against kinematic data from previous surgical procedures to identify arm movements performed at different stages of the surgical procedure and identify a step previously or presently performed by the robotic surgical device 214. In some examples, the procedure steps may be a complete list of movements of the robotic arms 226 as described above with respect to the image mapping device 600. In some examples, the procedure steps may be a general list of actions to be performed by the surgeon without specific robotic arm 226 movements.

At block 716, the computing device 204 displays the procedure steps and the image-mapped feature model at the display device 218 of the surgical console 212. The procedure steps and image-mapped feature model may each be presented at the display 218 as graphical elements overlaid on top of the image data 234 from the camera 230. As described above with respect to the image mapping device 600, the display may include indications or the progress of a surgery such as identifying a portion of anatomy yet to be removed or displaying a portion of anatomy already removed during the surgical procedure.

FIG. 8 illustrates an example flow chart depicting a process 800 for generating a feature model and updating the feature model based on additional depth data and image data gathered during a surgical procedure. The process 800 is performed by the computing device 204 and may be performed by the image mapping device 600.

The process 800 begins at block 802 with the computing device 204 receiving image data 234 from the camera 230, specifically a first image depicting an area including and surrounding the surgical site. The image data 234 may include images from a stereo camera or may include a single image or a stream of sequential images. In some examples, such as when the camera 230 is a stereoscopic camera that functions as the depth sensor 244, the image data from the camera 230 may also include depth data, as described above with respect to FIG. 3. In some examples, such as when a dedicated depth sensor 244 is provided, the process 800 may also include the computing device 204 receiving the depth data from the depth sensor.

At block 804, in addition to receiving the image data 234, the computing device 204 receives kinematic data from the robotic surgical device 214. The kinematic data may describe the current position or orientation of the robotic arms 226. The kinematic data received at block 802 may be descriptive of the robotic arm 226D to which the camera 230 is connected.

At block 806, after receiving the depth data corresponding to the surgical site, the computing device 204 generates a feature model of the patient anatomy surrounding the surgical site based on the image data 234 and the depth data 242. The feature model may also be generated based on the kinematic data, such as the arm data 240. The feature model is generated by the computing device 204 as described above with respect to the modeling device 500 and may include three-dimensional modeling techniques known in the art based on the data received by the computing device 204.

At block 808 the computing device 204 receives second image data from the camera 230. The second image data may be gathered after the camera 230 has been moved or rotated to view the patient anatomy from a different angle or to gather a larger field of view of the patient anatomy. Block 808 may also include receiving second kinematic data describing the new position or orientation of the camera 230 as it has been moved.

At block 810 the computing device 204 updates the feature model based on the second image data. The feature model may be incomplete or a partial model, such as a shell that is incomplete on one side, after receiving the first image data and the second image data may further refine and add to the feature model by capturing a different view of the anatomy or may refine the feature model by providing additional detail. The additional depth data and image data gathered with the second image data.

At block 812 the computing device 204 displays the feature model at the display device 218, and may generate a graphical element to include with the image data 234 from the camera 230 to display the feature model on the same display as the image data 234. The feature model may also have preoperative or intraoperative image data mapped onto it to provide a complete, up-to-date, real view of the feature model.

A portion of the process 800 may be repeated following block 812, including further refining and developing the feature model, or updating the feature model as the anatomy changes throughout a surgical procedure. Additional image data 234 and depth data 242 may be gathered and used to update and refine the feature model.

FIG. 9 illustrates an example flow chart depicting a process 900 for generating a image-mapped feature model of patient anatomy, according to at least one example. The process 900 is performed by the computing device 204.

The process 900 begins at block 902 by the computing device 204 receiving procedure data. The procedure data relates to the surgical procedure to be performed by the robotic surgical device 214 and may be received from a user through a user input device of the surgical console 212 or from database 202 where it was previously stored. The procedure data includes data such as the type of procedure (e.g., appendectomy, laparotomy, laparoscopy). The procedure data may include information such as arm data, patient anatomy models, and robotic arm placements during a previous surgical procedure. At block 902, the computing device 204 may receive data similarly to blocks 702 and 802 above.

At block 904 the computing device 204 receives preoperative data from the database 202. The preoperative data includes preoperative image data such as x-rays or other imaging performed prior to the operation. The preoperative image data may correspond to location of a future surgical site. In some examples, a user may use the computing device 204 to request the preoperative data. In some examples, depending on the procedure data received at block 702 and a patient identifier, the computing device 204 may automatically request the preoperative data relating to the patient and the particular procedure to be performed.

At block 906 the computing device 204 receives image data 234 from the camera 230 depicting an area surrounding the surgical site. The image data 234 may include images from a stereo camera or may include a single image or a stream of sequential images. In some examples, such as when the camera 230 is a stereoscopic camera that functions as the depth sensor 244, the image data from the camera 230 may also include depth data, as described above with respect to FIG. 3. In some examples, such as when a dedicated depth sensor 244 is provided, the process 900 may also include the computing device 204 receiving the depth data from the depth sensor 244.

At block 908, in addition to receiving the image data 234, the computing device 204 receives kinematic data from the robotic surgical device 214. The kinematic data may describe the current position or orientation of the robotic arms 226. The kinematic data received at block 908 may be descriptive of the robotic arm 226D to which the camera 230 is connected.

At block 910, after receiving the depth data, the computing device 204 generates a feature model of the patient anatomy surrounding the surgical site based on the image data 234 and the depth data 242. The feature model may also be generated based on the kinematic data, such as the arm data 240. The feature model is generated by the computing device 204 as described above with respect to the modeling device 500 and may include three-dimensional modeling techniques known in the art based on the data received by the computing device 204.

At block 912, the computing device 204 maps the preoperative data to the feature model generated in block 910. This is performed by the computing device 204 performing image mapping or image registration techniques known to those with skill in the art as described above with respect to the image mapping device 600. Block 912 may include the computing device 204 mapping, based on feature detection, edge detection, region-mapping, or any other known image mapping technique known in the art. At block 912, the computing device 204 maps the preoperative data to generate an image-mapped feature model. In some examples, the image data 234 may also be mapped to the feature model, providing an up-to-date image-mapped feature model of the patient anatomy.

At block 914 the computing device 204 displays the image-mapped feature model at the display device 218 of the surgical console 212. The image-mapped feature model may be presented at the display 218 as a graphical element overlaid on top of the image data 234 from the camera 230. As described above with respect to the image mapping device 600, the display may include indications or the progress of a surgery such as identifying a portion of anatomy yet to be removed or displaying a portion of anatomy already removed during the surgical procedure.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems may be embodied in a variety of other forms; furthermore, various omissions, substitutions and changes in the form of the methods and systems may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed in this description are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings described above in software to be used in programming or configuring a computing device.

Conditional language used above, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included above are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described above are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described above may be configured differently than described. For example, elements may be added to, removed from, or rearranged compared to the disclosed examples.

What is claimed is:

1. A computer-implemented method, comprising:
   receiving procedure type data describing a surgical procedure to be performed;
   receiving first image data corresponding to preoperative imaging of a surgical location, the surgical location based on the procedure type data;
   receiving second image data from a camera connected to a robotic arm of a robotic surgical system;
   receiving kinematic data describing a position and orientation of the robotic arm in relation to the surgical location;
   generating a feature model of the surgical location based on the image data and the kinematic data;
   generating an image-mapped feature model by mapping the first image data onto the feature model;
   determining a sequence of procedure steps based on the procedure type data and the image-mapped feature model;
   determining a current status of the surgical procedure based on the image-mapped feature model and current kinematic data using a pattern recognition algorithm, wherein the image-mapped feature model represents a first portion of anatomy yet to be removed and a second portion of anatomy that has already been removed; and
   providing, for display at a display device, (i) the sequence of procedure steps, and (ii) the current status of the surgical procedure, using the image-mapped feature model, by showing a first representation of the first portion of anatomy yet to be removed and a second representation of the second portion of anatomy that has already been removed, wherein the second representation of the second portion of anatomy that has already been removed comprises a shadow portion of the image-mapped feature model.

2. The computer-implemented method of claim 1, wherein determining the sequence of procedure steps comprises:
   accessing a database of procedure steps; and
   selecting the sequence of procedure steps based on the procedure type data.

3. The computer-implemented method of claim 1, further comprising:
   determining, based on the second image data, a current procedure step of the sequence of procedure steps corresponding to a present stage of the procedure; and
   providing, for display at the display device, the current procedure step.

4. The computer-implemented method of claim 1, further comprising generating an augmented reality display including the image-mapped feature model and the sequence of procedure steps.

5. The computer-implemented method of claim 1, wherein mapping the first image data onto the feature model comprises:
   determining a first number of distinct points in the first image data;
   determining a second number of distinct points in the feature model; and
   mapping the first image data onto the feature model by correlating the first number of distinct points with the second number of distinct points.

6. The computer-implemented method of claim 1, wherein the second image data comprises distance data from a depth sensing device connected to the camera and corresponding to distances between the camera and features of the surgical location.

7. The computer-implemented method of claim 1, wherein the first image data comprises at least one of:
   magnetic resonance image data;
   radiography;
   ultrasound;
   magnetic particle imaging;
   computed tomography image data; or
   positron emission tomography image data.

8. The computer-implemented method of claim 1, wherein the second image data represents anatomy at the surgical location, the method further comprising, following a first procedure step of the sequence of procedure steps:
   acquiring third image data from the camera, the third image data representing a change in the anatomy at the surgical location;
   updating the feature model of the surgical location based on the third image data;
   generating an updated image-mapped feature model by mapping the third image data onto the feature model; and
   providing, for display at the display device, the updated image-mapped feature model.

9. The computer-implemented method of claim 1, further comprising determining the kinematic data using a kinematic model of the robotic arm.

10. The computer-implemented method of claim 1, wherein the robotic arm of the robotic surgical system is controlled by a robotic surgical console.

11. A robotic surgical system comprising:
    a plurality of robotic arms to perform a surgical procedure;
    a camera positioned on a first robotic arm of the plurality of robotic arms;
    a display device to display output from the camera;
    one or more processors; and
    one or more non-transitory computer-readable media comprising processor-executable instructions that, when executed by the one or more processors, cause the one or more processors to:
      receive procedure type data describing the surgical procedure to be performed by the robotic surgical system;
      receive first image data corresponding to preoperative imaging of a surgical location, the surgical location based on the procedure type data;
      receive second image data from the camera including a present field of view of the camera;
      receive kinematic data describing a position of an end of the first robotic arm in relation to the surgical location;
      generate a feature model of the surgical location based on the second image data and the kinematic data;
      generate an image-mapped feature model by mapping the first image data onto the feature model;
      determine a sequence of procedure steps based on the procedure type data and the image-mapped feature model; and
      determining a current status of the surgical procedure based on the image-mapped feature model and current kinematic data using a pattern recognition algorithm, wherein the image-mapped feature model represents a first portion of anatomy yet to be removed and a second portion of anatomy that has already been removed; and provide, for display at the display device, (i) the sequence of procedure steps, and (ii) the current status of the surgical procedure, using the image-mapped feature model, by showing a first representation of the first portion of anatomy yet to be removed and a second representation of the second portion of anatomy that has already been removed, wherein the second representation of the second portion of anatomy that has already been removed comprises a transparent portion of the image-mapped feature model.

12. The robotic surgical system of claim 11, wherein the camera is a stereoscopic endoscope.

13. The robotic surgical system of claim 11, wherein the camera comprises a depth sensing device.

14. The robotic surgical system of claim 13, wherein the depth sensing device is at least one of:

a second camera;

an ultrasound sensor;

a radio detection and ranging sensor; or a light detection and ranging sensor.

15. The robotic surgical system of claim 11, wherein mapping the first image data onto the feature model comprises performing iterative closest-point registration.

16. The robotic surgical system of claim 11, wherein determining the sequence of procedure steps comprises:

accessing a database of procedure steps; and selecting the sequence of procedure steps based on the procedure type data.

17. The robotic surgical system of claim 11, wherein the one or more non-transitory computer-readable media comprising the processor-executable instructions that, when executed by the one or more processors, further cause the one or more processors to:

determining, based on the second image data, a current procedure step of the sequence of procedure steps corresponding to a present stage of the procedure; and providing, for display at the display device, the current procedure step.

* * * * *